United States Patent [19]

Hirschberg

[11] Patent Number: 4,932,409
[45] Date of Patent: Jun. 12, 1990

[54] SEAL ELEMENT IN AN IMPLANTABLE MEDICAL APPARATUS

[75] Inventor: Jakub Hirschberg, Taeby, Sweden

[73] Assignee: Siemens Aktiengesellschaft, Berlin and Munich, Fed. Rep. of Germany

[21] Appl. No.: 341,477

[22] Filed: Apr. 21, 1989

[30] Foreign Application Priority Data

May 16, 1988 [DE] Fed. Rep. of Germany ....... 3816640

[51] Int. Cl.5 .............................................. A61N 1/00
[52] U.S. Cl. .................................................. 128/419 P
[58] Field of Search ............... 128/419 P; 251/214; 411/542, 544, 915; 222/229

[56] References Cited

U.S. PATENT DOCUMENTS

| | | | |
|---|---|---|---|
| 1,356,873 | 10/1920 | Monteath | 411/542 |
| 2,264,413 | 12/1941 | Siegerist | |
| 2,476,074 | 9/1945 | Unger | 411/915 |
| 3,259,404 | 7/1966 | Papenguth | |
| 3,362,276 | 1/1968 | Gould | 411/542 |
| 3,606,357 | 9/1971 | Yonkers | 411/542 |
| 3,788,185 | 1/1974 | Gutshall | 411/371 |
| 3,889,569 | 6/1975 | Fanciullo | 411/915 |
| 4,072,154 | 2/1978 | Anderson et al. | 128/419 P |
| 4,141,752 | 2/1979 | Shipko | 128/419 P |
| 4,240,467 | 12/1980 | Blatt et al. | 137/625.66 |
| 4,292,876 | 10/1981 | De Graan | 411/542 |
| 4,479,489 | 10/1984 | Tucci | 128/419 P |

Primary Examiner—Lee S. Cohen
Assistant Examiner—Scott Getzow
Attorney, Agent, or Firm—Hill, Van Santen, Steadman & Simpson

[57] ABSTRACT

A seal element for an opening in an implantable medical apparatus, which can be penetrated by a tool and which maintains a hermetic seal after removal of the tool, is in the form of a ring of resilient material, initially having a ring opening with the wall thickness of the ring being larger than the radius of the ring opening. The ring can be turned inside-out, whereby the ring opening is closed. The placement of the seal element in the opening in the implantable medical apparatus maintains the opening closed to form a seal, but permits insertion of a tool therethrough.

6 Claims, 2 Drawing Sheets

SEAL ELEMENT IN AN IMPLANTABLE MEDICAL APPARATUS

BACKGROUND OF THE INVENTION

1. Field of the Invention

The present invention is directed to a seal element consisting of elastic material suitable for use in an implantable medical apparatus.

2. Description of the Prior Art

A heart pacemaker is described in U.S. Pat. 4,141,752 as exemplifying an implantable medical apparatus of the type wherein a seal element must be provided. For fastening an electrode lead to the terminal portion of heart pacemaker, the terminal portions provided with a hole or bore in which a screw is received which fixes the proximal end of the lead in the terminal portion. The screw is provided with an elastic seal element which seals the opening of the hole. A screwdriver which penetrates the seal element in order to reach the screw is used for turning the screw. A disadvantage of this conventional seal element is that the point of penetration does not always close upon removal of the screwdriver, so that the integrity of the seal is no longer guaranteed, and body fluid may penetrate into the terminal portion. This may result in leakage currents so that the energy of the stimulation pulses, which are supplied to the patient via the distal end of the lead, is partially lost, and may no longer be sufficient for stimulation of the heart under certain circumstances. Additionally due to the leakage currents, tissue in the region of the terminal portion may be undesirably stimulated, resulting in muscle spasms which are uncomfortable for the patient. Moreover, due to the leakage currents, the sensing function of the pacemaker electrode is degraded. If the leak is opened and closed in sequence, for example due to physical movements, the pacemaker may incorrectly interpret this as a QRS complex or a P-wave, which may result in inhibition of the generation of stimulation pulses under certain circumstances, if the pacemaker is a demand pacer. Moreover, if the seal is not tight, blood may penetrate into the region surrounding the screw, and coagulate, so that it is difficult to loosen the screw if the pacemaker must be subsequently replaced.

SUMMARY OF THE INVENTION

It is an object of the present to provide a seal element for an implantable medical apparatus which is penetratable by a tool, and which subsequently reliably hermetically seals upon removal of the tool.

The above object is achieved in a seal element in the form of a ring consisting of elastic material having a central opening, with a wall thickness greater than the radius of the central opening. The ring can be turned inside-out, so that the cross-section of the wall closes the opening. As a result of the selected wall thickness and because the material comprising the seal element is itself not penetrated or damaged upon the insertion of a tool, a reliable seal is always present.

In one embodiment of the invention, the cross section of the ring wall decreases in the outward direction (the term "outward" meaning before the ring is turned inside-out). After the ring is turned inside-out, the surface which then becomes the outer surface is relatively broad and thus results in a good hold when received, for example, in a hole or bore of the medical device. At the same time, the central region of the ring which is turned inside-out is relatively thin, and thus can be easily penetrated by a tool.

DESCRIPTION OF THE PREFERRED EMBODIMENTS

Figure 1:
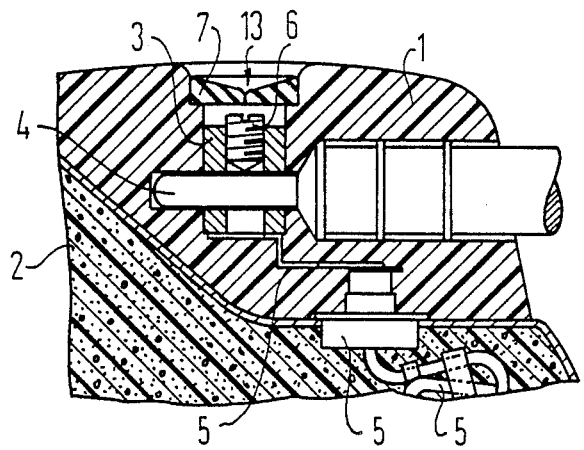
FIG. 1 is a side view of a portion of a pacemaker including a seal element constructed in accordance with the principles of the present invention.

The terminal portion 1 of heart pacemaker 2 is shown in section in FIG. 1. The terminal portion 1 includes a connecting bushing 3 into which the proximal end 4 of an electrode lead can be introduced. The connecting bushing 3 electrically connects the circuitry within the heart pacemaker 2 with the proximal end 4 of the lead. The electrical connection is referenced 5 in FIG. 1. The terminal portion 1 further includes a screw 6 for maintaining an electrical and mechanical connection of the proximal end 4 of the lead with the bushing 3. A seal element 7 is provided for sealing the opening in the terminal portion 1, so that no body fluid can enter into communication with the connecting bushing 3, or the screw 6, after implantation of the heart pacemaker in a patient.

Figure 2:
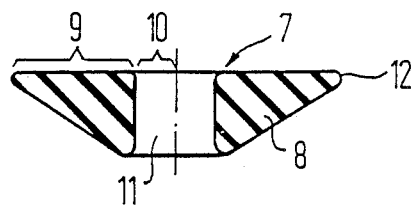
FIG. 2 is a side sectional view of the seal element used in the embodiment of FIG. 1, before turning the seal element inside-out.
Figure 3:
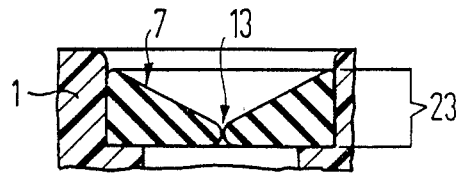
FIG. 3 is a side sectional view of the seal element of FIG. 2 turned inside-out and inserted in a receptacle in a medical device.

The seal element 7 is shown in section in FIG. 2. The seal element consists of elastic material, and is in the form of ring 8 having a wall thickness 9 which is greater than the radius 10 of the ring opening. The ring 8 can be turned inside-out, as shown in FIG. 3, so that its outer edge 12 is turned inward. As shown in FIG. 3, this causes the ring opening 11 to become closed. The ring 8 is retained in this inside-out configuration by the walls of the opening in the terminal portion 1 in which the seal element 7 is inserted. The seal element 7 still permits insertion of a tool, such as a screwdriver (not shown) through the central region 13 of the seal element 7, without damaging the elastic material. The central region 13 again closes after removal of the tool. Due to the size relationship between the wall thickness 9 and the ring opening 11, the broad outer surface 23 of the ring 8 is compressed with sufficient pressure so that the seal element 7 hermetically closes, and remains closed, after removal of the tool.

Further embodiments in different configurations of the seal element in accordance with the principles of the present invention are shown in FIGS. 4 through 9.

Figure 4:
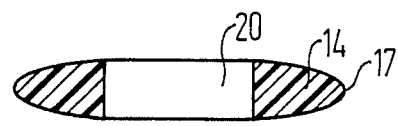
FIGS. 4 and 5 are side sectional views of another embodiment of a seal element in accordance with the principles of the present invention, before and after being turned inside-out.
Figure 5:
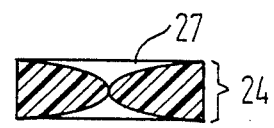

FIG. 4 shows a ring 14 having a cross section which is a portion of an oval, and which has an outer edge 17 and central opening 20. When the ring 14 is turned inside-out a seal element 27 is formed as shown in FIG. 5, having a relatively broad outer surface 24.

Figure 6:
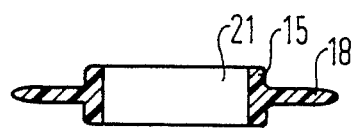
FIGS. 6 and 7 are side sectional views of a further embodiment of a seal element in accordance with the principles of the present invention, before and after being turned inside-out.
Figure 7:
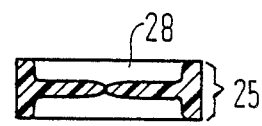

The ring 15 in the embodiment of FIG. 6 has a T-shaped cross section, with an outer edge 18 and a central opening 21. When a seal element 28 is formed by turning the ring 15 inside-out as shown in FIG. 7, a relatively broad outer surface 25 is formed, with the opening 21 being closed.

Figure 8:
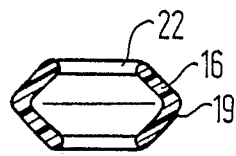
FIGS. 8 and 9 are side sectional views of another embodiment of a seal element in accordance with the principles of the present invention, before and after being turned inside-out.
Figure 9:
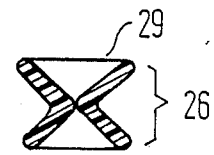

A ring 16 having a V-shaped cross section in FIG. 8, having an outer edge 19 and a central opening 22. Again, when a seal element 29 is formed by turning the ring 16 inside-out as shown in FIG. 9, a relatively broad outer surface 26 is formed.

In each of the embodiments of the rings shown in FIGS. 2, 4, 6 and 8, the cross section of the rings 8, 14, 15 and 16 decreases toward the outside, i.e., before the ring is turned inside-out. After each of the rings 8, 14, 15 and 16 are turned inside-out, the resulting outer surfaces 23, 24, 25 and 26 are relatively broad, permitting the seal element to be reliably secured in the opening of an implantable medical device. The central regions of the seal elements 7, 27, 28 and 29, by contrast, are relatively thin, thus facilitating penetration by a tool.

Although the seal element disclosed herein has been described in the context the a heart pacemaker, it will apparent that the seal element can be used in any type of implantable medical device wherein an opening must be sealed such as, for example, an infusion pump.

Although modifications and changes may be suggested by those skilled in the art it is the intention of the inventor to embody within the patent warranted hereon all changes and modifications as reasonable and properly come within the scope of his contribution to the art.

I claim as my invention:

1. An element for sealing an opening in an implantable medical apparatus comprising:

a ring consisting of resilient material and having an outer diameter and an inner diameter, said inner diameter defining a ring opening having a radius, and said inner diameter and said outer diameter defining a ring wall therebetween having a cross-section and a thickness, said thickness being larger than said radius of said ring opening and said cross section having a shape so that when said ring is turned inside-out said ring opening is tightly closed to form a liquid seal centrally penetrable by an instrument without rupturing said ring, and the inside-out ring is adapted to the received and held in said opening in said implantable medical device.

2. An element as claimed in claim 1, wherein said ring has a cross section decreasing from said inner diameter to said out diameter.

3. An element as claimed in claim 1, wherein said ring has a cross section which is a portion of an oval.

4. An element as claimed in claim 1, wherein said ring has a T-shaped cross section.

5. An element as claimed in claim 1, wherein said ring has a V-shaped cross section.

6. An element as claimed in claim 1, wherein said ring has triangular cross-section.

* * * * *